(12) United States Patent
Gu et al.

(10) Patent No.: US 7,368,085 B2
(45) Date of Patent: May 6, 2008

(54) ANALYTE DETECTOR

(75) Inventors: Yuandong Gu, St. Paul, MN (US); Son Thai Lu, Plymouth, MN (US)

(73) Assignee: Honeywell International Inc., Morristown, NJ (US)

( * ) Notice: Subject to any disclaimer, the term of this patent is extended or adjusted under 35 U.S.C. 154(b) by 727 days.

(21) Appl. No.: 10/727,891

(22) Filed: Dec. 4, 2003

(65) Prior Publication Data

US 2005/0123442 A1 Jun. 9, 2005

(51) Int. Cl.
*B32B 5/02* (2006.01)
*B32B 27/04* (2006.01)
*B32B 27/12* (2006.01)
*G01N 27/00* (2006.01)
*G01N 33/00* (2006.01)

(52) U.S. Cl. .............. 422/82.01; 422/50; 422/68.1; 422/82.02; 436/43; 436/149; 436/91; 436/95; 257/1; 257/20; 257/192; 257/213; 600/300; 600/319; 600/316; 600/317; 600/345; 600/347; 600/365

(58) Field of Classification Search ............ 422/50, 422/68.1, 82.01, 82.02; 436/43, 149, 91, 436/95; 257/1, 20, 192, 213; 600/300, 319, 600/316, 317, 345, 347, 365
See application file for complete search history.

(56) References Cited

U.S. PATENT DOCUMENTS

| 4,371,374 A | 2/1983 | Cerami et al. |
| 5,217,691 A | 6/1993 | Greene et al. |
| 5,244,562 A | 9/1993 | Russell |
| 5,474,552 A * | 12/1995 | Palti .............. 604/67 |
| 5,503,770 A | 4/1996 | James et al. |
| 5,543,024 A * | 8/1996 | Hanazato et al. ........... 257/253 |
| 6,063,637 A | 5/2000 | Arnold et al. |
| 6,201,980 B1 | 3/2001 | Darrow et al. |

(Continued)

OTHER PUBLICATIONS

Appleton et al., "Detection of Total sugar concentration using photoinduced electron transfer materials: development of operationally stable, reusable optical sensors," Sensors and Actuators B Chemical, pp. 302-304, 2000.

(Continued)

*Primary Examiner*—Brian Sines
(74) *Attorney, Agent, or Firm*—Kris T. Fredrick

(57) ABSTRACT

An analyte detector including a device having a surface, wherein the device is capable of detecting a charge adjacent to the surface. The surface includes a plurality of molecules bonded thereto, wherein the molecules have a structure (I):

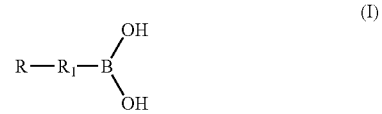

where R is a ligand bonded to the surface of the device and $R_1$ is a spacer having 5 to 50 carbon atoms. The charge adjacent to the surface is created by the anionic complex of structure (I), and the number of anionic complex of structure (I) is dependent on the concentration of the analyte of interest. Methods for detecting an analyte are also disclosed, as well as systems using such analyte detectors.

7 Claims, 5 Drawing Sheets

U.S. PATENT DOCUMENTS

| | | | |
|---|---|---|---|
| 6,319,540 B1 | 11/2001 | Van Antwerp et al. | |
| 6,475,750 B1* | 11/2002 | Han et al. | 435/14 |
| 6,484,045 B1 | 11/2002 | Holker et al. | |
| 6,602,678 B2 | 8/2003 | Kwon et al. | |
| 7,049,645 B2* | 5/2006 | Sawada et al. | 257/292 |
| 2005/0265914 A1* | 12/2005 | Gu et al. | 423/445 B |

OTHER PUBLICATIONS

Cary et al., "Ruthenium bipyridine complexes for the recognition of glucose," Sensors and Actuators B Chemical, pp. 25-32, 2002.

Chiang et al., "Study of the pH-ISFET and EnFET for Biosensor Applications," Journal of Medical and Biological Engineering, pp. 135-146, 2001.

DiCesare et al., "Charge transfer fluorescent probes using boronic acids for monosaccharide signaling," Journal of Biomedical Optics, vol. 7 No. 4, pp. 538-545, Oct. 2002.

Dzyadevich et al., "Application of enzyme field-effect transistors for determination of glucose concentrations in blood serum," Biosensors & Bioelectronics 14, pp. 283-287, 1999.

Shoji et al., "Poly(aniline boronic acid): A new Precursor to Substituted Poly(aniline)s," American Chemical Society, vol. 17, No. 23, 3 pages, Nov. 13, 2001.

Shul'ga et al., "Overall characterization of ISFET-based glucose biosensor," Sensors and Actuators B. 10, pp. 41-46, 1992.

Yin et al., "Glucose ENFET doped with $MnO_2$ powder," Sensors and Actuators B Chemical 76, pp. 187-192, 2001.

* cited by examiner

ANALYTE DETECTOR

FIELD OF THE INVENTION

The present invention generally relates to the field of analyte detectors, and more particularly, to analyte detectors capable of detecting polyhydroxylated compounds such as glucose.

BACKGROUND OF THE INVENTION

Many different devices and methods are presently being used to measure the concentration of various sugars and amino acids in a wide variety of solutions. Many industrial manufacturing and food processing systems require that the level of one or more sugars and/or amino acids be carefully monitored at various stages to help insure the desired quality of final products. For example, the varying glucose concentrations during fermentation processes are important process control parameters, and their continuous monitoring can improve the yield and quality of the fermentation product. In addition, there are a large number of situations where the amount of sugar in finished food stuffs and other sugar containing products must be determined. On line continuous measurement is important in reducing the risk of contamination, labor costs and delays associated with off-line measurements. To be able to perform on-line measurements, there is a need for sterilizable sensors with rapid response times and high sensitivity, yet which also require minimum maintenance and calibration.

One important use for sugar analysis techniques is in the medical field where monitoring of sugar levels in biological fluids is desirable for the proper diagnosis and treatment of diabetes and other diseases. With respect to medical applications, glucose is by far the most important sugar, and diabetes is the most common disease for which glucose determinations are routinely conducted. Diabetes is a disease of the metabolic system that affects more than 14 million people in the United States and over 100 million people worldwide. It is characterized by an elevated blood-glucose concentration which is caused by a lack of the hormone insulin. Sugars are the primary source of metabolic energy, and the inability to self-regulate the levels of sugar metabolized by the body leads to many other medical problems, including but not limited to blindness, heart disease and kidney failure.

The one-time or 'spot' measurement of blood-glucose concentration ex vivo is also not optimal, as it requires collection of a blood sample, usually obtained by pricking the finger, which must be done at least several times each day. To avoid the need to subject the patient to this painful process for glucose monitoring, much effort has gone into identifying alternative sources for samples, such as subcutaneous tissue fluid, urine or saliva instead of blood, and for identifying less-painful and more efficient ways to obtain these samples, such as by transdermal extraction or using very thin needles. The development of new, highly sensitive and miniaturizable glucose monitoring technology will make some of these alternative methods more feasible for use at home by patients.

Treatment of diabetes involves monitoring of the patient's blood-glucose levels, with insulin injections being given when the glucose concentration rises above normal levels. A simple and accurate method for measuring blood-glucose concentrations is an essential cornerstone of any diabetes treatment protocol, since excessively low blood-glucose levels in diabetes patients can result in coma and even death. Frequent testing and insulin administration can significantly reduce long-term complications of diabetes. The vast majority of sensors which are used currently for glucose monitoring are based on enzymes such as glucose oxidase or glucose dehydrogenase. These enzyme-based sensors are simple to use and have relatively high sensing selectivity. They are widely used for one-time measurement of blood-glucose concentrations ex vivo. However, among the many drawbacks of enzyme-based sensors are that they are costly and have a short life time. This inherently unstable enzyme must be protected from extreme conditions during manufacturing and storage in order to preserve its catalytic activity. In addition, there have been a number of problems associated with the use of enzymes in implantable sensors used in systems for continuously monitoring blood-glucose levels in vivo, among them the fact that enzymes can elicit an immune response and are not stable to most sterilization methods. The development of non-enzymatic approaches to glucose sensing is desirable in order to provide more effective management of diabetes, both for spot monitoring of glucose concentrations as well as for in vivo continuous monitoring.

A few nonenzymatic methods for measuring glucose have been proposed as alternatives to the above-described enzyme-based devices. U.S. Pat. No. 5,217,691 describes the use of boronic acids for the semiquantitative colorimetric determination of glucose. U.S. Pat. No. 4,371,374 discloses separating and quantitating glycosylated amino acids, peptides or mixtures thereof by treating a urine sample with a suitable boronic acid to complex the glycosylated compounds, separating them and analyzing the separated complexed material. U.S. Pat. No. 5,503,770 discloses a fluorescent boronic acid conjugate which emits fluorescence upon binding to saccharides. U.S. Pat. No. 5,244,562 discloses switching devices coated with a polymer imprinted with glucose and boronic acid.

Although some of the above-described sensors have shown promise, none have been found to be entirely satisfactory. There is a continuing need to develop robust sensor systems that can be used to simply, accurately, and rapidly measure the amount of a particular sugar, amino acid or related compound which is present in solutions and other environments. The need is particularly apparent with respect to ex vivo and in vivo glucose determinations which can be an important component in medical diagnosis and treatment of various metabolic disorders, including diabetes. There is also a strong need to develop robust sensor technology for real-time monitoring of sugars, amino acids and other metabolites in manufacturing process environments.

SUMMARY OF THE INVENTION

The present invention generally relates to an analyte detector that includes a device that is capable of detecting a charge adjacent to a surface. In one illustrative embodiment, a plurality of molecules, each bonded to the surface of the device, are provided to generate a charge adjacent to the surface, where the amount of charge generated by the molecules is related to a concentration of an analyte to be detected. In one illustrative embodiment, the molecules have a structure (I):

(I)

where, R is a ligand bonded to the surface of the device and $R_1$ is a spacer having 5 to 50 carbon atoms. In another illustrative embodiment, the molecules have a structure (II):

(II)

where, R is a ligand bonded to the gate surface, $R_2$ is a ($C_{14}$-$C_{24}$) alkylene, or ($C_{14}$-$C_{24}$) alkenylene, and $R_3$ is an ($C_3$-$C_{14}$) cycloalkylene, ($C_3$-$C_{14}$) heterocyclylene, ($C_3$-$C_{24}$) arylene, or ($C_3$-$C_{14}$) heteroarylene. In some illustrative embodiments, the device can include a field effect transistor with a surface between the source and drain, and a monolayer of molecules bonded to the surface. The charge adjacent to the surface may activate the field effect transistor to produce a source-drain current that is related to the charge adjacent the surface, and thus the concentration of the analyte of interest.

In another illustrative embodiment of the present invention, a method is described for detecting an analyte. The method includes the steps of bonding a plurality of molecules to a surface of a device, wherein the device is capable of detecting a charge provided adjacent to the surface. In some embodiments, the molecules may have a structure (I):

(I)

where, R is a ligand bonded to the surface of the device, and $R_1$ is a spacer having 5 to 50 carbon atoms. An anionic complex is formed with an analyte and the molecule of structure (I). A charge is generated adjacent to the surface by the anionic complex, and the number anionic complex (and thus charge) is dependent on the concentration of the analyte of interest. The charge is then detected, and in some cases electrically amplified, by the device. Systems using such detectors are also contemplated and disclosed.

BRIEF DESCRIPTION OF THE DRAWINGS

The invention may be more completely understood in consideration of the following detailed description of various embodiments of the invention in connection with the accompanying drawings, in which.

While the invention is amenable to various modifications and alternative forms, specifics thereof have been shown by way of example in the drawings and will be described in detail. It should be understood, however, that the intention is not to limit the invention to the particular illustrative embodiments described. On the contrary, the intention is to cover all modifications, equivalents, and alternatives falling within the spirit and scope of the invention.

DETAILED DESCRIPTION OF THE INVENTION

The following description should be read with reference to the drawings, in which like elements in different drawings are numbered in like fashion. The drawings, which are not necessarily to scale, depict selected embodiments and are not intended to limit the scope of the invention. Although examples of construction, dimensions, and materials may be illustrated for the various elements, those skilled in the art will recognize that many of the examples provided have suitable alternatives that may be utilized.

The present invention provides an analyte detector and methods for the determination of biological levels of polyhydroxylated compounds, particularly glucose. In some embodiments, the invention uses a device or system that is insertable or even implantable, and which produces a signal of detection, such as external to the skin of a mammal, for example, a human. Detection of the signal produced by the analyte detector determines the quantity of polyhydroxylated compound or analyte of interest. While the present invention is not so limited, an appreciation of various aspects of the invention will be gained through a discussion of the various illustrative embodiments and examples provided below.

As used herein, the term "alkylene" refers to a straight or branched chain divalent hydrocarbon radical optionally containing one or more heteroatomic substitutions independently selected from S, O, Si, or N. Alkylene groups generally include those with one to twenty atoms. Alkylene groups may be unsubstituted or substituted with those substituents that do not interfere with the specified function of the composition. Substituents include alkoxy, hydroxy, mercapto, amino, alkyl substituted amino, or halo, for example. Examples of "alkylene" as used herein include, but are not limited to, methylene, ethylene, propane-1,3-diyl, propane-1,2-diyl and the like.

As used herein, the term "alkenylene" refers to a straight or branched chain divalent hydrocarbon radical having one or more carbon——carbon double bonds and optionally containing one or more heteroatomic substitutions independently selected from S, O, Si, or N. Alkenylene groups generally include those with one to twenty atoms. Alkenylene groups may be unsubstituted or substituted with those substituents that do not interfere with the specified function of the composition. Substituents include alkoxy, hydroxy, mercapto, amino, alkyl substituted amino, or halo, for example. Examples of "alkenylene" as used herein include, but are not limited to, ethene-1,2-diyl, propene-1, 3-diyl, and the like.

As used herein, the term "cycloalkylene" refers to an alicyclic divalent hydrocarbon radical. Cycloalkylene groups generally include those with three to twelve carbon atoms. Cycloalkylene groups may be unsubstituted or substituted with those substituents that do not interfere with the specified function of the composition. Substituents include alkoxy, hydroxy, mercapto, amino, alkyl substituted amino, or halo, for example. Such a cycloalkylene ring may be optionally fused to one or more of another heterocyclic ring(s), heteroaryl ring(s), aryl ring(s), cycloalkenyl ring(s), or cycloalkyl rings. Examples of "cycloalkylene" as used herein include, but are not limited to, cyclopropyl-1,1-diyl, cyclopropyl-1,2-diyl, cyclobutyl-1,2-diyl, cyclopentyl-1,3-diyl, cyclohexyl-1,2-diyl, cyclohexyl-1,3-diyl cyclohexyl-1,4-diyl, cycloheptyl-1,4-diyl, or cyclooctyl-1,5-diyl, and the like.

As used herein, the term "heterocyclylene" refers to a divalent three to twelve membered non-aromatic heterocyclic ring radical containing one or more heteroatoms independently selected from S, O, or N and having zero to five degrees of unsaturation. Heterocyclylene groups may be unsubstituted or substituted with those substituents that do not interfere with the specified function of the composition. Substituents include alkoxy, hydroxy, mercapto, amino, alkyl substituted amino, or halo, for example. Such a heterocyclylene ring may be optionally fused to one or more of another heterocyclic ring(s), heteroaryl ring(s), aryl ring(s), cycloalkenyl ring(s), or cycloalkyl rings. Examples of "heterocyclylene" as used herein include, but are not limited to, tetrahydrofuran-2,5-diyl, morpholine-2,3-diyl, pyran-2,4-diyl, 1,4-dioxane-2,3-diyl, 1,3-dioxane-2,4-diyl, piperidine-2,4-diyl, piperidine-1,4-diyl, pyrrolidine-1,3-diyl, morpholine-2,4-diyl, and the like.

As used herein, the term "arylene" refers to divalent unsaturated aromatic carbocyclic radicals having a single ring, such as phenylene, or multiple condensed rings, such as naphthylene or anthrylene. Arylene groups may be unsubstituted or substituted with those substituents that do not interfere with the specified function of the composition. Substituents include alkoxy, hydroxy, mercapto, amino, alkyl substituted amino, or halo, for example. Such an "arylene" ring may be optionally fused to one or more of another heterocyclic ring(s), heteroaryl ring(s), aryl ring(s), cycloalkenyl ring(s), or cycloalkyl rings. Examples of "arylene" as used herein include, but are not limited to, benzene-1,2 diyl, benzene-1,3-diyl, benzene-1,4-diyl, naphthalene-1,8-diyl, anthracene-1,4-diyl, and the like.

As used herein, the term "heteroarylene" refers to a divalent five- to seven-membered aromatic ring radical containing one or more heteroatoms independently selected from S, O, or N. Heteroarylene groups may be unsubstituted or substituted with those substituents that do not interfere with the specified function of the composition. Substituents include alkoxy, hydroxy, mercapto, amino, alkyl substituted amino, or halo, for example. Such a "heteroarylene" ring may be optionally fused to one or more of another heterocyclic ring(s), heteroaryl ring(s), aryl ring(s), cycloalkenyl ring(s), or cycloalkyl rings. Examples of "heteroarylene" used herein include, but are not limited to, furan-2,5-diyl, thiophene-2,4-diyl, 1,3,4-oxadiazole-2,5-diyl, 1,3,4-thiadiazole-2,5-diyl, 1,3-thiazole-2,4-diyl, 1,3-thiazole-2,5-diyl, pyridine-2,4-diyl, pyridine-2,3-diyl, pyridine 2,5-diyl, pyrimidine-2,4-diyl, quinoline-2,3-diyl, and the like.

In an illustrative embodiment, an analyte detector can include a device having a surface, wherein the device is capable of detecting a charge adjacent the surface. One illustrative device is a Field Effect Transistor (FET). In the case of a FET, the surface may be between the source and drain, and when a charge is provided adjacent the surface, the FET may be activated to produce a corresponding current between the source and drain, where the magnitude of the source-drain current may represent the quantity of charge adjacent the surface. A plurality of molecules are provided on the surface for generating a charge adjacent the surface that is related to the concentration of the analyte of interest. For example, a plurality of molecules capable of forming a stable anionic complex with a polyhydroxylated compound such as, for example, glucose may be bonded to the surface. In some embodiments, the molecules have a structure (I):

where, R is a ligand capable of bonding to the surface to the device, and $R_1$ is a spacer having 5 to 50 carbon atoms or 10 to 50 carbon atoms.

The ligand R can be covalently bonded to the surface of the device. The ligand can be capable of bonding the molecule of structure (I) to a variety of inorganic materials such as, for example, gold, silver, copper, lead, tantalum oxide, silicon oxide, zirconium oxide, tin oxide, or group III-IV semiconductors, or mixtures thereof. In some embodiments, the ligand can be a thiol, siloxane, or phosphate. For example, a thiol ligand can bond to conductive metals such as, for example, gold, silver or copper. A siloxane ligand can bond, for example, to silicon oxide or glass. A phosphate or phosphonate ligand can bond, for example, to tantalum oxide, zirconium oxide or tin oxide. Thus, the ligand can be selected, depending on the material forming the surface of the device.

In an illustrative embodiment, the spacer $R_1$ can have 14 to 24 carbon atoms or 14, 15, 16, 17, 18, 19, or 20 carbon atoms. $R_1$ may be a ($C_{14}$-$C_{24}$) alkylene, ($C_{14}$-$C_{24}$) alkenylene, ($C_{14}$-$C_{24}$) cycloalkylene, ($C_{14}$-$C_{24}$) heterocyclylene, ($C_{14}$-$C_{24}$) arylene, or ($C_{14}$-$C_{24}$) heteroarylene. For example, $R_1$ may be a ($C_{14}$-$C_{20}$) alkylene, or ($C_{14}$-$C_{20}$) alkenylene. In an illustrative embodiment, the spacer can be 2 nm to 4 nm in length.

In another illustrative embodiment, the plurality of molecules capable of forming a stable anionic complex with a polyhydroxylated compound can have a structure (II):

where, R is a ligand bonded to the gate surface, $R_2$ is a ($C_{10}$-$C_{24}$) alkylene, or ($C_{10}$-$C_{24}$) alkenylene, and $R_3$ is an ($C_3$-$C_{14}$) cycloalkylene, ($C_3$-$C_{14}$) heterocyclylene, ($C_3$-$C_{24}$) arylene, or ($C_3$-$C_{14}$) heteroarylene. In one embodiment $R_2$ is a ($C_{10}$-$C_{20}$) alkylene. In another embodiment, $R_3$ is a phenylene or naphthalene. The molecule of structure (II) can be a spacer described as $R_1$ that is equal to the $R_2$ and $R_3$ moiety.

Illustrative embodiments of the molecule of structure (I) and (II) include:

The boronic acid moiety can be in the ortho, meta, or para position on the phenyl ring for any of the compounds shown above.

The molecules having structure (I) or structure (II) are capable of forming a stable anionic complex with a polyhydroxylated compound such as, for example, glucose. A proposed glucose binding mechanism for molecules having structure (I) is described as:

R and $R_1$ are described above. A proposed glucose binding mechanism for molecules having structure (II) is described as:

Although not being bound by any particular theory, it is believed that the mechanism of boronic acid's moiety polyol sensitivity is that the anionic form of the boronic acid moiety can form covalent complexes with molecules having diol groups held in a coplanar configuration, such as a cis-2 diol or cis-3 diol molecule, for example, glucose. Binding of the diol to the anionic boronic acid moiety stabilizes the anionic boronic acid moiety. The net outcome of this reversible binding between glucose and the anionic boronic acid moiety is the increase of the fraction of negatively charged boronic acid, which forms a charge adjacent to the surface of the device.

The molecules shown in FIGS. 1-5 illustrate R' as a spacer moiety as described above. In addition, R' is defined as both ($R_1$) and ($R_2$-$R_3$) all defined above. The molecules discussed below correspond to the molecules of structure (I) and structure (II) described above.

Figure 1:
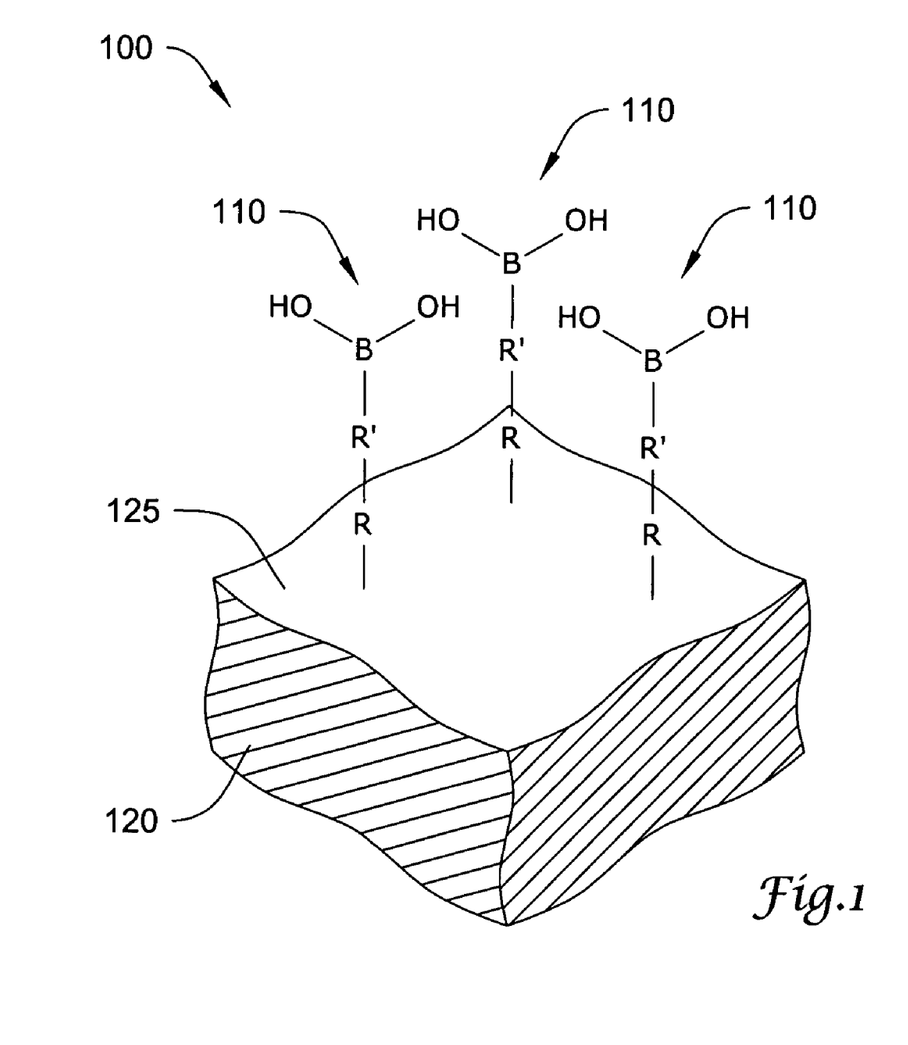
FIG. 1 is a schematic view of a plurality of molecules bonded to a device surface.

FIG. 1 is a schematic view of a detector 100 having a plurality of molecules 110 bonded to a surface 125 of a device 120, where the device 120 is capable of detecting a charge adjacent to the surface. In one illustrative embodiment, the device 120 can be a Field Effect Transistor (FET), and the surface 125 is between the source and drain of the FET. When so provided, it is contemplated that the surface may be the surface of a conductive gate electrode, the surface of a gate oxide or other insulating layer, or the semiconductor surface of the FET itself. When the surface is the semiconductor surface of the FET itself, the plurality of molecules that are bonded to the surface may be electrically insulating, with the charge generated by the chemical interaction being spaced from the semiconductor surface of the FET.

In an illustrative embodiment, the plurality of molecules can be molecules having structure (I) and/or structure (II) as described above. These molecules can be covalently bonded to the surface 125 via the ligand group R, as described above. In an illustrative embodiment, these molecules 110 can form a monolayer on at least a portion of the surface 125. The molecules 110 can be oriented substantially or generally orthogonal (i.e. extending away from the surface 125 at any angle) to the surface 125. The boronic acid moiety of the molecule 110 can extend away from the surface 125. The surface 125 can be formed of a variety of materials such as, for example, gold, silver, copper, lead, tantalum oxide, silicon oxide, zirconium oxide, tin oxide, or group III-IV semiconductors, or mixtures thereof.

Figure 2:
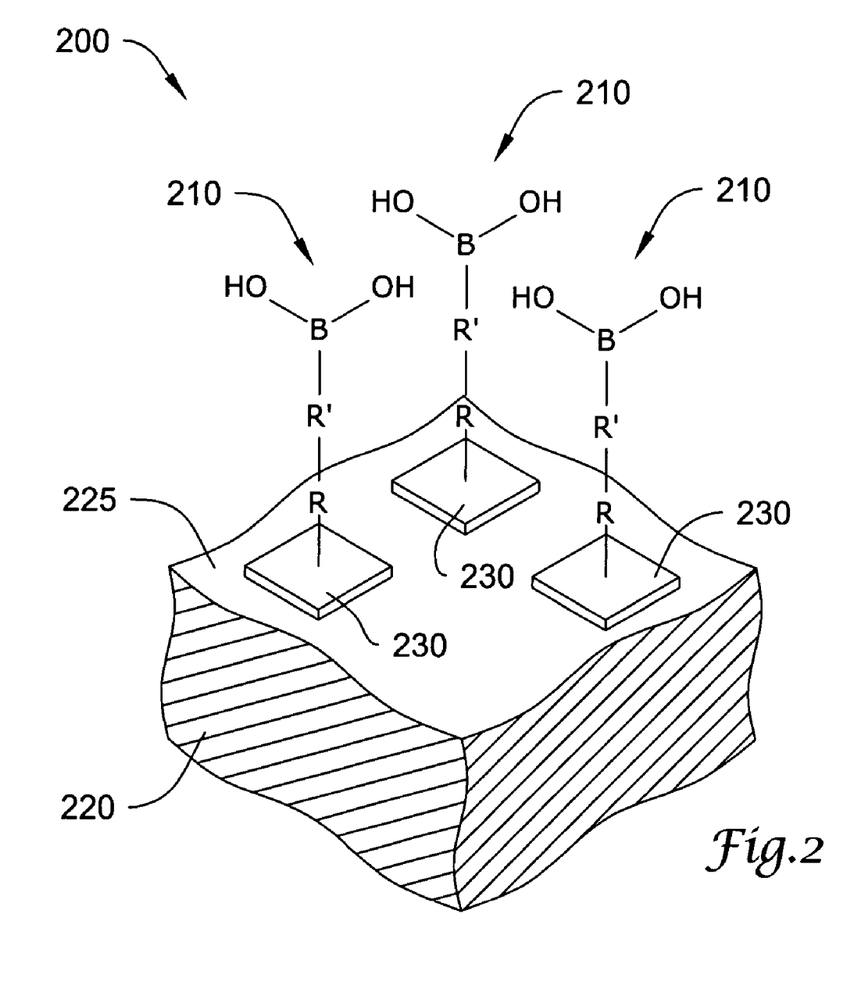
FIG. 2 is a schematic view of a plurality of molecules bonded to a conductive metal layer disposed on a device surface.

FIG. 2 is a schematic view of a plurality of molecules 210 bonded to a conductive metal layer 230 disposed on a surface 225 of a device 220. Device 220 may function as described above. When the device 220 is a FET device, the conductive metal layer may, for example, form the gate of the FET or be provided above the gate of the FET. To help the electric field produced by the charge generated by the interaction of the plurality of molecules with the analyte of interest reach the channel of the FET, it is contemplated that the conductive metal layer may be non-continuous. The gaps between the conductive metal layer islands 230 may provide a path for the electric field to reach the channel. In some cases, the non-continuous conductive metal layer has a fill factor of less than 90%, less than 80%, less than 70%, less than 60%, or less than 50%, depending on the application. The conductive metal layer 230 can be deposited, and optionally patterned, on the surface 225 using any number of known techniques. In one example, the metal layer may laid down so thin that, after processing, the result is a non-continuous metal layer that includes a number of islands, as described above. In another example, the conductive metal layer 230 may be patterned using photolithography. The conductive metal layer 230 can be any useful thickness such as, for example, 0.5 to 50 nm, or 3 to 10 nm. The metal layer 230 can be one or more metals and can include one or more layers, as desired.

In an illustrative embodiment, molecules 210 are bonded to the patterned metal layer 230 and not bonded to the surface 225, thus the molecules 210 can form a monolayer only on the islands of the metal layer 230. In this embodiment, the non-continuous metal layer 230 will allow much of the electric field produced by the charge generated by the interaction between the plurality of molecules and the analyte of interest to reach and modulate the channel of a FET, or to be detected by some other detecting device.

Figure 3:
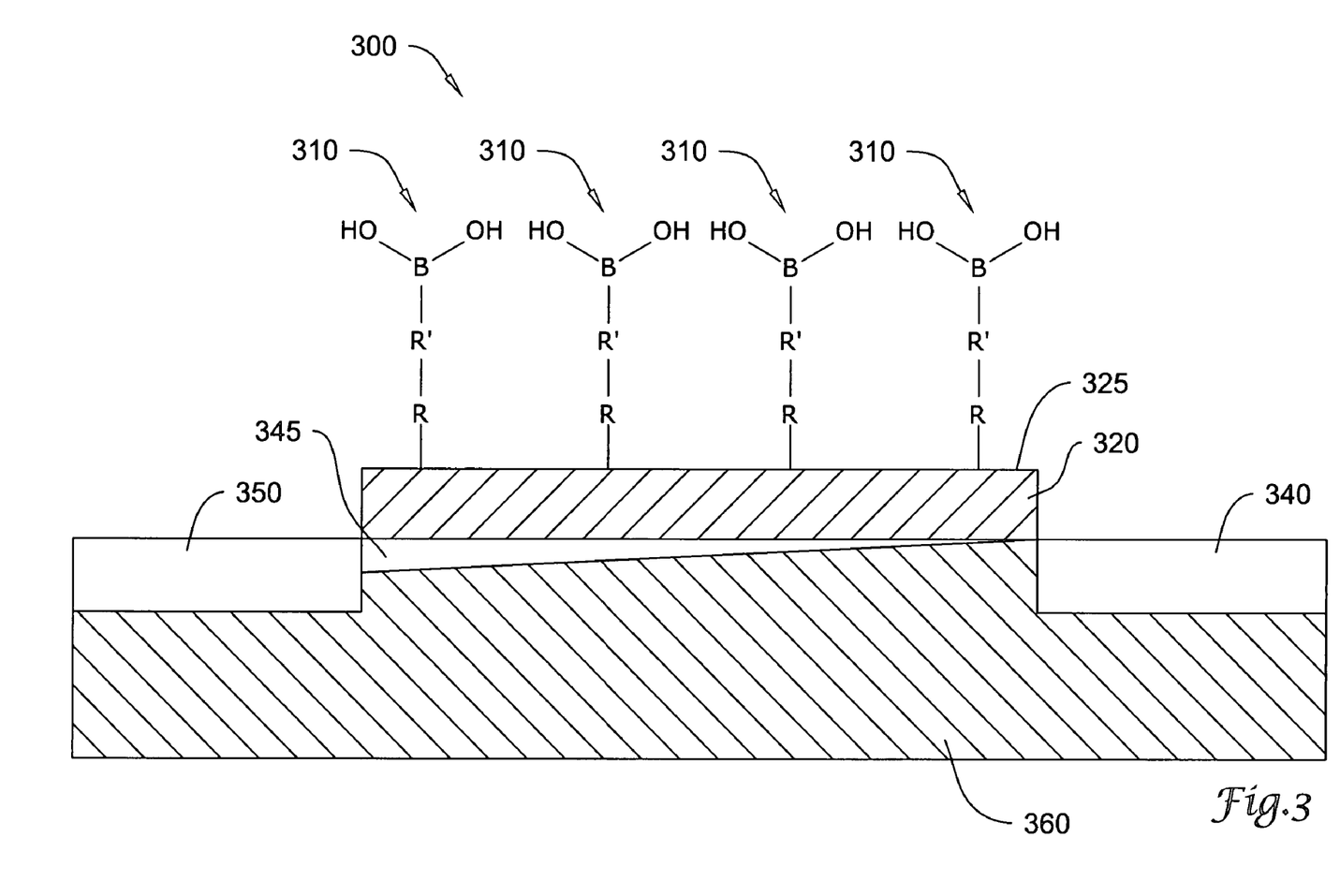
FIG. 3 is a schematic view of a plurality of molecules bonded to a gate surface of a field effect transistor.

FIG. 3 is a schematic view of a plurality of molecules 310 bonded to a gate surface 325 of a Field Effect Transistor (FET) 300. In an illustrative embodiment, the FET 300 includes a gate 320 having a gate surface 325, a source 350, drain 340, a substrate 360, and a channel 345 below the gate 320. The FET of FIG. 3 can be any type of field effect type device, including an enhancement mode or depletion mode device, as desired.

Figure 4:
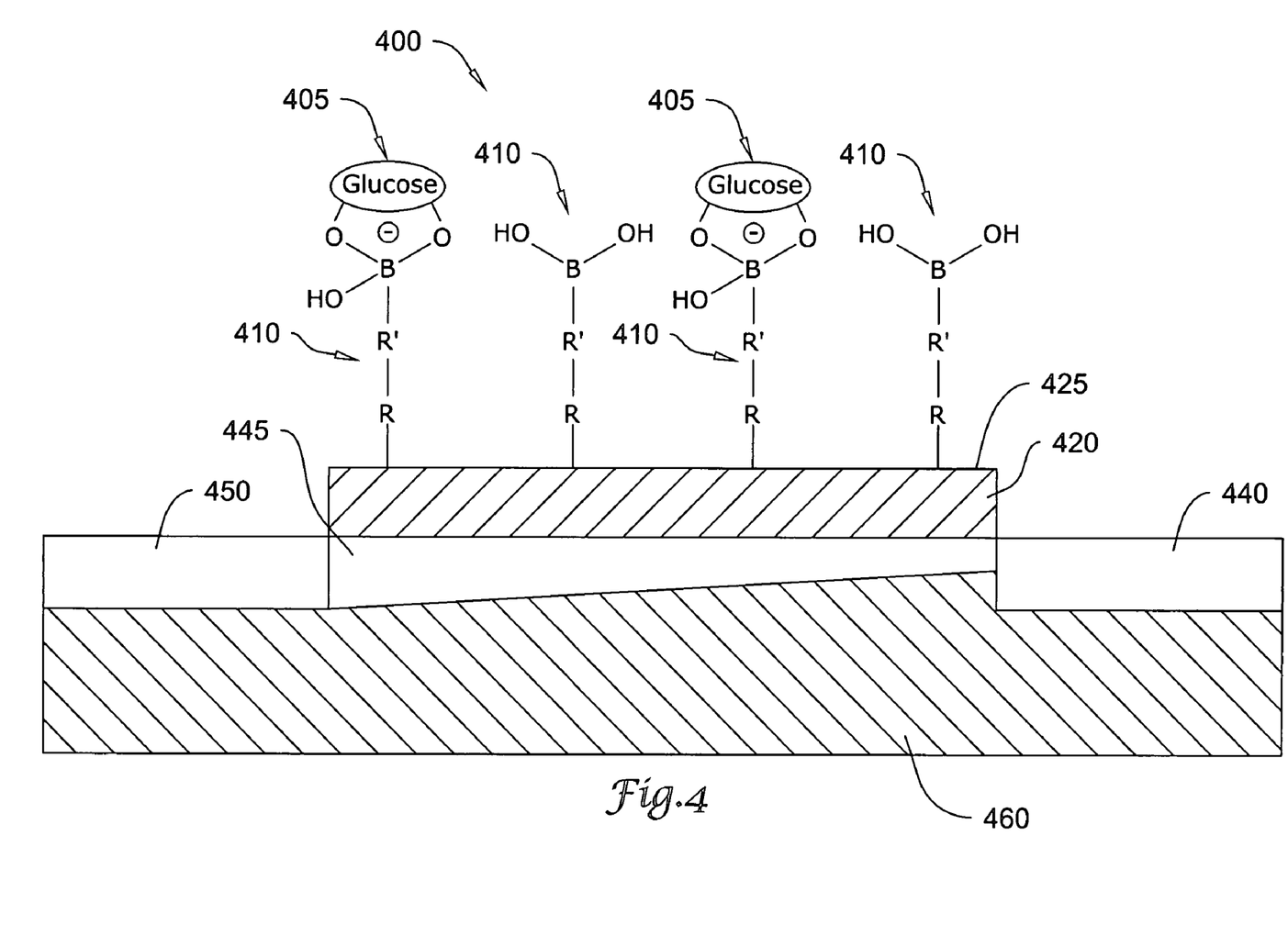
FIG. 4 is a schematic view of a plurality of molecules bonded to a gate surface of a field effect transistor and binding to target analytes.

FIG. 4 is a schematic view of a plurality of molecules 410 bonded to a gate surface 425 of a field effect transistor 400 and binding to target analytes 405. The target analytes 405 illustrated are glucose. The target analytes reversible binding mechanism to the boronic acid moiety is described above. Like the FET in FIG. 3, FET 400 can include a gate 420 having a gate surface 425, a source 450, a drain 440, a substrate 460, and a channel 445 below the gate 420. In this illustrative embodiment, the FET 400 may be a p-type enhancement mode device.

For a given FET, and when properly biased, the source-drain current ($I_{sd}$) is related to the gate-source voltage ($V_{gs}$). For an enhancement mode device, when little charge is present adjacent to the gate as shown in FIG. 3, the chemically induced gate-source voltage is small, and the channel 345 is relatively narrow, thereby producing a lower source-drain current ($I_{sd}$). However, and as shown in FIG. 4, binding a diol such as, for example glucose, increases the charge adjacent to the gate area 420 of the FET, which decreases the gate-source voltage, which in turn, widens the channel 445 and increases the source-drain current of a P-channel FET device. Such a change in the source drain current may be used as a measure of the diol concentration of the solution under test. Although not explicitly shown in FIGS. 3 and 4, if the gates 320 and 420 are conductive, it may be desirable to provide a field path through the conductive gate so that the electric field produced by the charge 411 can more easily reach and modulate the channel 445 of the FET.

In another illustrative embodiment, a feedback path is used to keep the gate-source voltage constant. The amount of feedback required to do this may provide a measure of the diol concentration of the solution under test. This may be accomplished in any number of ways. In one illustrative embodiment, a constant source-drain current is provided to the drain of the FET via a constant current source or the like. As charge accumulates on the gate—because of the binding of the diol—the voltage on the gate changes. The change in gate voltage causes a change in the drain voltage. In one illustrative embodiment, an amplifier or the like senses the drain voltage, and provides a feed back signal to the gate of the FET through the solution under test. The feedback signal cancels out the change in gate voltage caused by the binding of the diol. The feedback signal thus provides a measure of the diol concentration of the solution under test.

Figure 5:
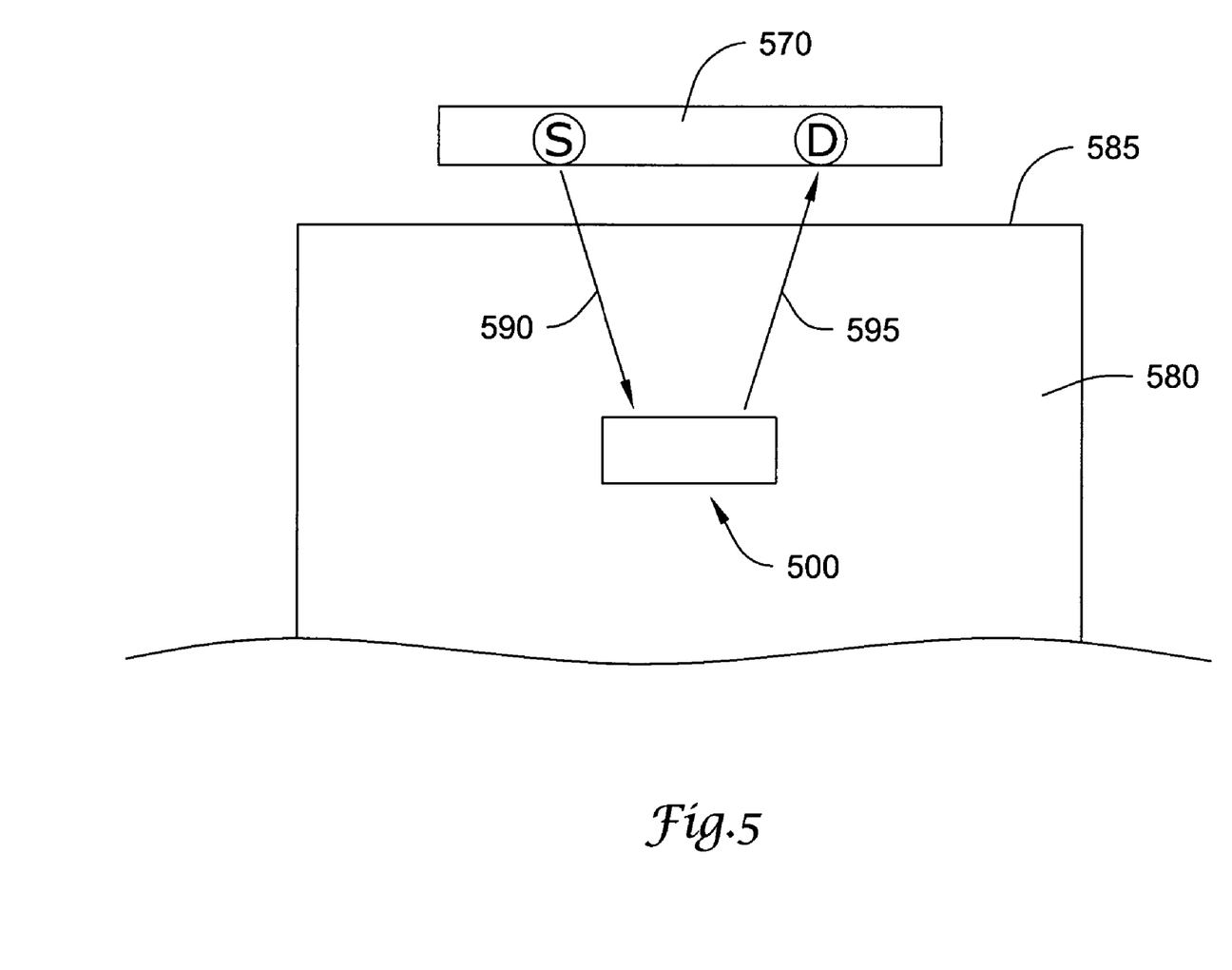
FIG. 5 is a schematic view of an in vivo chemical detector cooperating with an ex vivo interrogator.

FIG. 5 is a schematic view of an in vivo chemical sensor 500 cooperating with an ex vivo interrogator 570. The basic scheme utilizes both an interrogator module 570 which can be external to the skin 585. The interrogator may provide an excitation signal 590 which interrogates a subcutaneous analyte detector system 500. In some cases, the subcutaneous analyte detector system 500 may include a power source such as a battery. In other cases, the subcutaneous analyte detector system 500 may not include a power source, but rather may receive a wireless power signal from the interrogator. The subcutaneous analyte detector system 500 may include one or more of the analyte sensors described above. The subcutaneous analyte detector system 500 may produce a signal 595 that is related to the concentration of the analyte of interest, and provide the signal to an external detector in the interrogator 570.

It is contemplated that the subcutaneous analyte detector system 500 can be implanted into a variety of tissues 580. In an illustrative embodiment, the subcutaneous analyte detector system 500 may be implanted subcutaneously at a depth of from 1 to 2 mm below the surface of the skin. At this depth, the subcutaneous analyte detector system 500 is easily implanted between the dermis layer and the subcutaneous fat layer. In mammals, these layers are relatively easily separated and the subcutaneous analyte detector system 500 can be inserted into a small pocket created in a minor surgical procedure. The implanted subcutaneous analyte detector system 500 can be profused by capillary blood. Alternatively, the subcutaneous analyte detector system 500 can be placed in contact with other fluids containing the analyte of interest.

The subcutaneous analyte detector system 500 can operate in vivo at a normal in vivo pH range such as, from 5 to 8. In some illustrative embodiments, the subcutaneous analyte detector system 500 has a glucose detection range from 0.036 mg/dL to 900 mg/dL or from 30 mg/dL to 500 mg/dL, but any other suitable range may also be used, depending on the application.

EXAMPLES

All of the starting materials described herein are commercially available from a variety of sources such as, Aldrich Chemical (Milwaukee, Wis.) or readily synthesized using conventional methods. Illustrative molecules that are suitable for forming a monolayer on a device surface are synthesized below. A variety of additional molecules can be synthesized using the scheme below by simply varying the starting materials as is known. Two illustrative thiols and two illustrative phosphates are described below.

Thiol Molecules

-continued

Formation of Molecule Monolayer

A four inch silicon wafer with a layer of SiO$_2$ on top, is cleaned with hot piranha bath (110° C.), cleaned with DI water, and baked at 110° C. for 1 minute.

A portion of the silicon wafer is then coated with a 100 Å titanium layer and then a 1000 Å gold layer is deposited on the titanium layer using known deposition techniques.

The silicon wafer is then diced into 1 cm×5 cm pieces with half of each die covered with titanium/gold and half of it is bare silicon.

The titanium/gold coated silicon pieces are soaked in a diluted boiling piranha solution (1:4 H$_2$O$_2$/H$_2$SO$_4$) for 1 minute. The titanium/gold coated silicon pieces are then rinsed thoroughly with water, H$_2$O$_2$, water, and then dried in a jet of N$_2$.

The dried titanium/gold coated silicon pieces are dipped in 1 mM thiolated phenylboronic acid (see thiol molecules above) solutions (deoxygenated with N$_2$ or Ar) at room temperature avoiding light.

The thiol molecules attach to the gold layer and form a monolayer of molecules.

The present invention should not be considered limited to the particular examples described above, but rather should be understood to cover all aspects of the invention as fairly set out in the attached claims. Various modifications, equivalent processes, as well as numerous structures to which the present invention can be applicable will be readily apparent to those of skill in the art to which the present invention is directed upon review of the instant specification.

What is claimed is:

1. An analyte detector comprising:
   a field effect transistor having a gate surface; and
   a monolayer of molecules, each molecule bonded to the gate surface, the molecules having a structure (II):

wherein,
R is a ligand bonded to the gate surface;
R$_2$ is a (C$_{10}$-C$_{24}$) alkylene, or (C$_{10}$-C$_{24}$) alkenylene; and
R$_3$ is an (C$_3$-C$_{14}$) cycloalkylene, (C$_3$-C$_{14}$) heterocyclylene, (C$_3$-C$_{24}$) arylene, or (C$_3$-C$_{14}$) heteroarylene.

2. The analyte detector according to claim 1, wherein R$_2$ is a (C$_{10}$-C$_{20}$) alkylene.

3. The analyte detector according to claim 1, wherein $R_3$ is a phenylene or naphthalene.

4. The analyte detector according to claim 1, wherein the ligand is thiol, phosphate, or siloxane.

5. The analyte detector according to claim 1, wherein the gate surface is a conducting surface.

6. The analyte detector according to claim 1, wherein the gate surface is a non-continuous conducting surface of the field effect transistor, and the monolayer of molecules form a non-conducting layer on the non-continuous conducting surface.

7. The analyte detector according to claim 1, wherein the gate surface is an insulating surface.

* * * * *